(12) United States Patent
Cerrina et al.

(10) Patent No.: US 6,375,903 B1
(45) Date of Patent: Apr. 23, 2002

(54) METHOD AND APPARATUS FOR SYNTHESIS OF ARRAYS OF DNA PROBES

(75) Inventors: Francesco Cerrina; Michael R. Sussman; Frederick R. Blattner; Sangeet Singh-Gasson; Roland Green, all of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/253,460

(22) Filed: Feb. 22, 1999

Related U.S. Application Data
(60) Provisional application No. 60/075,641, filed on Feb. 23, 1998, now abandoned.

(51) Int. Cl.[7] .......................... B32B 27/04; B01J 10/00; C12Q 1/68; C12M 1/00; C07H 21/00
(52) U.S. Cl. ..................... 422/131; 422/129; 422/134; 422/149; 422/186; 422/188; 422/189; 422/190; 422/193; 422/211; 422/219; 422/232; 435/283.1; 435/286.1; 435/286.2; 435/286.4; 435/286.5; 435/289.1; 435/292.1; 435/299.1; 435/305.1; 435/6; 530/333; 530/334; 536/25.3
(58) Field of Search .......................... 422/50, 62, 68.1, 422/69, 129, 131, 134, 149, 186, 188, 189, 190, 193, 211, 219, 232; 435/6, 283.1, 286.1, 286.2, 286.4, 286.5, 289.1, 292.1, 299.1, 305.1; 536/25.3; 530/333, 334

(56) References Cited

U.S. PATENT DOCUMENTS

| | | | |
|---|---|---|---|
| 4,146,329 A | * 3/1979 | King et al. | 356/152 |
| 4,163,150 A | 7/1979 | Stankewitz | 250/205 |
| 4,301,363 A | * 11/1981 | Suzuki et al. | 250/216 |
| 4,571,603 A | 2/1986 | Hornbeck et al. | 346/160 |

(List continued on next page.)

FOREIGN PATENT DOCUMENTS

| | | |
|---|---|---|
| EP | 0 961 174 A2 | 12/1999 |
| WO | WO 93/22678 | 11/1993 |
| WO | WO 99/41007 | 8/1999 |
| WO | WO 99/63385 | 12/1999 |

OTHER PUBLICATIONS

A. Offner, "New Concepts in Projection Mask Aligners," Optical Engineering, vol. 14, pp. 130–132 (1975).

R.T. Kerth, et al., "Excimer Laser Projection Lithography on a Full–Field Scanning Projection System," IEEE Electron Device Letters, vol. EDL–7(5), pp. 299–301 (1986).

(List continued on next page.)

Primary Examiner—Ardin H. Marschel
(74) Attorney, Agent, or Firm—Foley & Lardner

(57) ABSTRACT

The synthesis of arrays of DNA probes sequences, polypeptides, and the like is carried out using a patterning process on an active surface of a substrate. An image is projected onto the active surface of the substrate utilizing an image former that includes a light source that provides light to a micromirror device comprising an array of electronically addressable micromirrors, each of which can be selectively tilted between one of at least two positions. Projection optics receives the light reflected from the micromirrors along an optical axis and precisely images the micromirrors onto the active surface of the substrate, which may be used to activate the surface of the substrate. The first level of bases may then be applied to the substrate, followed by development steps, and subsequent exposure of the substrate utilizing a different pattern of micromirrors, with further repeats until the elements of a two dimensional array on the substrate surface have an appropriate base bound thereto. The micromirror array can be controlled in conjunction with a DNA synthesizer supplying appropriate reagents to a flow cell containing the active substrate to control the sequencing of images presented by the micromirror array in coordination of the reagents provided to the substrate.

31 Claims, 14 Drawing Sheets

U.S. PATENT DOCUMENTS

| | | |
|---|---|---|
| 4,596,992 A | 6/1986 | Hornbeck ............... 346/76 PH |
| 4,615,595 A | 10/1986 | Hornbeck .................. 353/122 |
| 4,662,746 A | 5/1987 | Hornbeck .................. 350/269 |
| 5,028,939 A | 7/1991 | Hornbeck et al. .......... 346/160 |
| 5,096,279 A | 3/1992 | Hornbeck et al. .......... 359/230 |
| 5,143,854 A | 9/1992 | Pirrung et al. .............. 436/518 |
| 5,202,231 A | 4/1993 | Drmanac et al. .............. 435/6 |
| 5,252,743 A | 10/1993 | Barrett et al. ............ 548/303.7 |
| 5,318,679 A | 6/1994 | Nishioka ............... 204/157.68 |
| 5,324,483 A | 6/1994 | Cody et al. .................. 422/131 |
| 5,405,783 A | 4/1995 | Pirrung et al. .............. 436/518 |
| 5,412,087 A | 5/1995 | McGall et al. ............. 536/24.3 |
| 5,424,186 A | 6/1995 | Fodor et al. .................... 435/6 |
| 5,445,934 A | 8/1995 | Fodor et al. .................... 435/6 |
| 5,451,683 A | 9/1995 | Barrett et al. ............ 548/302.7 |
| 5,482,867 A | 1/1996 | Barrett et al. ............... 436/518 |
| 5,489,678 A | 2/1996 | Fodor et al. ............... 536/22.1 |
| 5,504,614 A | 4/1996 | Webb et al. ................ 359/223 |
| 5,510,270 A | 4/1996 | Fodor et al. ................ 436/518 |
| 5,535,047 A | 7/1996 | Hornbeck ................... 359/295 |
| 5,556,752 A | 9/1996 | Lockhart et al. ............... 435/6 |
| 5,578,832 A | 11/1996 | Trulson et al. ........... 250/458.1 |
| 5,583,688 A | 12/1996 | Hornbeck ................... 359/291 |
| 5,593,839 A | 1/1997 | Hubbell et al. ................ 435/6 |
| 5,599,695 A | 2/1997 | Pease et al. ............... 435/91.1 |
| 5,600,383 A | 2/1997 | Hornbeck ................... 348/771 |
| 5,631,734 A | 5/1997 | Stern et al. ................. 356/317 |
| 5,653,939 A | 8/1997 | Hollis et al. .................. 422/50 |
| 5,677,195 A | 10/1997 | Winkler et al. ............. 436/518 |
| 5,695,940 A | 12/1997 | Drmanac et al. ............... 435/6 |
| 5,744,305 A | 4/1998 | Fodor et al. .................... 435/6 |
| 5,753,788 A | 5/1998 | Fodor et al. ............... 536/22.1 |
| 5,768,009 A | 6/1998 | Little .......................... 359/293 |
| 5,831,070 A | 11/1998 | Pease et al. ................ 536/25.3 |
| 6,271,957 B1 | 8/2001 | Quate et al. ................. 359/298 |
| 6,295,153 B1 | 9/2001 | Garner ........................ 359/212 |

OTHER PUBLICATIONS

F.N. Goodall, et al., "Excimer Laser Photolithography with 1:1 Wynne–Dyson Optics," SPIE vol. 922, Optical/Laser Microlithography, 1988.

B. Ruff, et al., "Broadband Deep–UV High NA Photolithography System," SPIE vol. 1088, Optical/Laser Microlithography II (1989).

Larry J. Hornbeck, "Digital Light Processing and MEMs: Reflecting the Digital Display Needs of the Networked Society," SPIE/EOS European Symposium on Lasers, Optics, and Vision for Productivity and Manufacturing I, Besancon, France, Jun. 10–14, 1996.

McGall, et al., "Light–Directed Synthesis of High–Density Oligonucleotide Arrays Using Semiconductor Photoresists," Proc. Natl. Acad. Sci. USA, vol. 93, pp. 13555–13560, Nov. 1996.

G.H. McGall, et al., "The Efficiency of Light–Directed Synthesis of DNA Arrays on Glass Substrates," Journal of the American Chemical Society 119, No. 22, 1997, pp. 5081–5090.

Pease, et al., Light–generated oligonucleotide arrays for rapid DNA sequence analysis. Proc. Natal. Acad. Sci. USA. May 1994, vol. 91, pp. 5022–5026.

John A. Neff, et al., "Two–Dimensional Spatial Light Modulators: A Tutorial," Proceedings of The IEEE, vol. 78, No. 5, May 1990, pp. 826–855.

* cited by examiner

METHOD AND APPARATUS FOR SYNTHESIS OF ARRAYS OF DNA PROBES

CROSS REFERENCE TO RELATED APPLICATION

This application claims the benefit of provisional patent application No. 60/075,641, filed Feb. 23, 1998; now abandoned.

This invention was made with United States government support awarded by the following agencies: DOE Grant Nos.: DE-FG07-96ER13938; P0062242-02; DE-FG02-96ER45569; 63040304; P071760302; NSF Grant Nos.: IBN-9706552; ECS-9317745; INT-960289; ONR DOD-Navy Grant# N00014-97-1-0460; DOD-Army Grant# DAAH04-95-1-0456; USDA AGRICCREE Grant No.: 95-37304-2364. The United States has certain rights in this invention.

FIELD OF THE INVENTION

This invention pertains generally to the field of biology and particularly to techniques and apparatus for the analysis and sequencing of DNA and related polymers.

BACKGROUND OF THE INVENTION

The sequencing of deoxyribonucleic acid (DNA) is a fundamental tool of modern biology and is conventionally carried out in various ways, commonly by processes which separate DNA segments by electrophoresis. See, e.g., Current Protocols In Molecular Biology, Vol. 1, Chapter 7, "DNA Sequencing," 1995. The sequencing of several important genomes has already been completed (e.g., yeast, *E. coli*), and work is proceeding on the sequencing of other genomes of medical and agricultural importance (e.g., human, C. elegans, Arabidopsis). In the medical context, it will be necessary to "re-sequence" the genome of large numbers of human individuals to determine which genotypes are associated with which diseases. Such sequencing techniques can be used to determine which genes are active and which inactive either in specific tissues, such as cancers, or more generally in individuals exhibiting genetically influenced diseases. The results of such investigations can allow identification of the proteins that are good targets for new drugs or identification of appropriate genetic alterations that may be effective in genetic therapy. Other applications lie in fields such as soil ecology or pathology where it would be desirable to be able to isolate DNA from any soil or tissue sample and use probes from ribosomal DNA sequences from all known microbes to identify the microbes present in the sample.

The conventional sequencing of DNA using electrophoresis is typically laborious and time consuming. Various alternatives to conventional DNA sequencing have been proposed. One such alternative approach, utilizing an array of oligonucleotide probes synthesized by photolithographic techniques is described in Pease, et al., "Light-Generated Oligonucleotide Arrays for Rapid DNA Sequence Analysis," Proc. Natl. Acad. Sci. USA, Vol. 91, pp. 5022–5026, May 1994. In this approach, the surface of a solid support modified with photolabile protecting groups is illuminated through a photolithographic mask, yielding reactive hydroxyl groups in the illuminated regions. A 3' activated deoxynucleoside, protected at the 5' hydroxyl with a photolabile group, is then provided to the surface such that coupling occurs at sites that had been exposed to light. Following capping, and oxidation, the substrate is rinsed and the surface is illuminated through a second mask to expose additional hydroxyl groups for coupling. A second 5' protected activated deoxynucleoside base is presented to the surface. The selective photodeprotection and coupling cycles are repeated to build up levels of bases until the desired set of probes is obtained. It may be possible to generate high density miniaturized arrays of oligonucleotide probes using such photolithographic techniques wherein the sequence of the oligonucleotide probe at each site in the array is known. These probes can then be used to search for complementary sequences on a target strand of DNA, with detection of the target that has hybridized to particular probes accomplished by the use of fluorescent markers coupled to the targets and inspection by an appropriate fluorescence scanning microscope. A variation of this process using polymeric semiconductor photoresists, which are selectively patterned by photolithographic techniques, rather than using photolabile 5' protecting groups, is described in McGall, et al., "Light-Directed Synthesis of High-Density Oligonucleotide Arrays Using Semiconductor Photoresists," Proc. Natl. Acad. Sci. USA, Vol. 93, pp. 13555–13560, November 1996, and G. H. McGall, et al., "The Efficiency of Light-Directed Synthesis of DNA Arrays on Glass Substrates," Journal of the American Chemical Society 119, No. 22, 1997, pp. 5081–5090.

A disadvantage of both of these approaches is that four different lithographic masks are needed for each monomeric base, and the total number of different masks required are thus four times the length of the DNA probe sequences to be synthesized. The high cost of producing the many precision photolithographic masks that are required, and the multiple processing steps required for repositioning of the masks for every exposure, contribute to relatively high costs and lengthy processing times.

SUMMARY OF THE INVENTION

In accordance with the present invention, the synthesis of arrays of DNA probe sequences, polypeptides, and the like is carried out rapidly and efficiently using patterning processes. The process may be automated and computer controlled to allow the fabrication of a one or two-dimensional array of probes containing probe sequences customized to a particular investigation. No lithographic masks are required, thus eliminating the significant costs and time delays associated with the production of lithographic masks and avoiding time-consuming manipulation and alignment of multiple masks during the fabrication process of the probe arrays.

In the present invention, a substrate with an active surface to which DNA synthesis linkers have been applied is used to support the probes that are to be fabricated. To activate the active surface of the substrate to provide the first level of bases, a high precision two-dimensional light image is projected onto the substrate, illuminating those pixels in the array on the substrate active surface which are to be activated to bind a first base. The light incident on the pixels in the array to which light is applied deprotects OH groups and makes them available for binding to bases. After this development step, a fluid containing the appropriate base is provided to the active surface of the substrate and the selected base binds to the exposed sites. The process is then repeated to bind another base to a different set of pixel locations, until all of the elements of the two-dimensional array on the substrate surface have an appropriate base bound thereto. The bases bound on the substrate are protected, either with a chemical capable of binding to the bases or with a layer(s) of photoresist covering all of the bound bases, and a new array pattern is then projected and imaged onto the substrate to activate the protecting material in those pixels to which the first new base is to be added. These pixels are then exposed and a solution containing the selected base is applied to the array so that the base binds at the exposed pixel locations. This process is then repeated for all of the other pixel locations in the second level of bases. The process as described may then be repeated for each desired level of bases until the entire selected two-dimensional array of probe sequences has been completed.

The image is projected onto the substrate utilizing an image former having an appropriate light source that provides light to a micromirror device comprising a two-dimensional array of electronically addressable micromirrors, each of which can be selectively tilted between one of at least two separate positions. In one of the positions of each micromirror, the light from the source incident on the micromirror is deflected off an optical axis and away from the substrate, and in a second of the at least two positions of each micromirror, the light is reflected along the optical axis and toward the substrate. Projection optics receive the light reflected from the micromirrors and precisely image the micromirrors onto the active surface of the substrate. Collimating optics may be used to collimate the light from the source into a beam provided directly to the micromirror array or to a beam splitter, wherein the beam splitter reflects a portion of the beam to the micromirror array and transmits reflected light from the micromirror array through the beam splitter. The light directly reflected from the micromirrors or transmitted through the beam splitter is directed to projection optics lenses which image the micromirror array onto the active surface of the substrate. Because the selectively addressable micromirrors in the micromirror array may either fully reflect or fully deflect the light provided to them, the image of the micromirror array exhibits a very high contrast between the "on" and "off" pixels. The micromirrors may also be capable of being indexed to more than two positions, in which case additional optics may be provided to allow exposure of more than one substrate using a single micromirror array device. In addition, the micromirrors are capable of reflecting light at any wavelength without damage to them, allowing short wavelength light, including light in the range of ultraviolet to near ultraviolet light, to be utilized from the light source.

The micromirror array is operated under control of a computer which provides appropriate pixel address signals to the micromirror array to cause the appropriate micromirrors to be in their "reflect" or "deflect" positions. The appropriate micromirror array pattern for each activation step in each level of bases to be added to the probes is programmed into the computer controller. The computer controller thus controls the sequencing of the images presented by the micromirror array in coordination with the reagents provided to the substrate.

In one embodiment, the substrate may be transparent, allowing the image of the micromirror array to be projected through the surface of the substrate that is opposite to the active surface. The substrate may be mounted within a flow cell, with an enclosure sealing off the active surface of the array, allowing the appropriate reagents to be flowed through the flow cell and over the active surface of the array in the appropriate sequence to build up the probes in the array.

Further objects, features and advantages of the invention will be apparent from the following detailed description when taken in conjunction with the accompanying drawings.

DETAILED DESCRIPTION OF THE INVENTION

Figure 1:
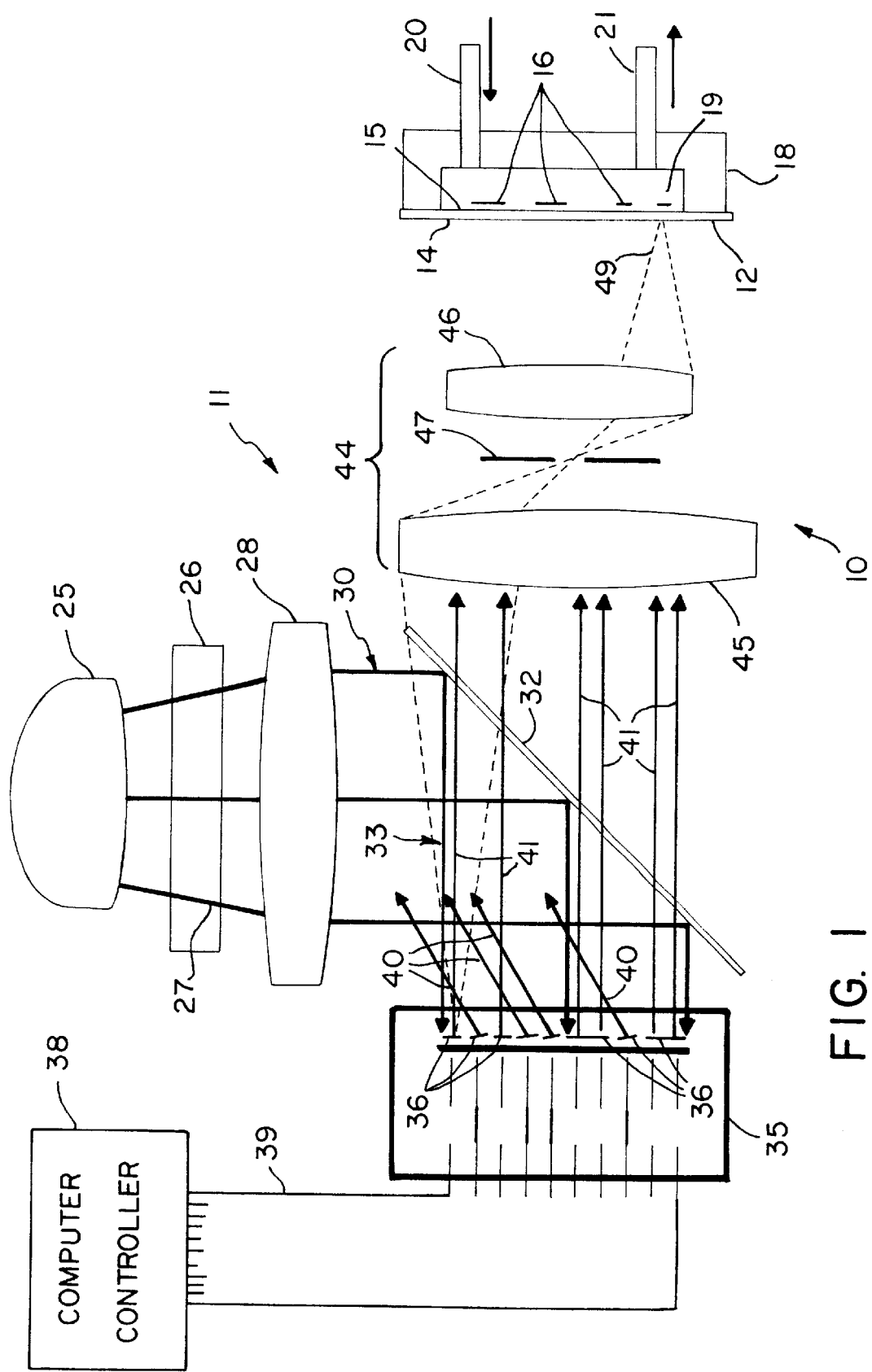
FIG. 1 is a schematic view of an array synthesizer apparatus in accordance with the present invention.

With reference to the drawings, an exemplary apparatus that may be used for DNA probe array synthesis, polypeptide synthesis, and the like is shown generally at 10 in FIG. 1 and includes a two-dimensional array image former 11 and a substrate 12 onto which the array image is projected by the image former 11. For the configuration shown in FIG. 1, the substrate has an exposed entrance surface 14 and an opposite active surface 15 on which a two-dimensional array of nucleotide sequence probes 16 are to be fabricated. For purposes of illustration, the substrate 12 is shown in the figure with a flow cell enclosure 18 mounted to the substrate 12 enclosing a volume 19 into which reagents can be provided through an input port 20 and an output port 21. However, the substrate 12 may be utilized in the present system with the active surface 15 of the substrate facing the image former 11 and enclosed within a reaction chamber flow cell with a transparent window to allow light to be projected onto the active surface. The invention may also use an opaque or porous substrate. The reagents may be provided to the ports 20 and 21 from a conventional base synthesizer (not shown in FIG. 1).

The image former 11 includes a light source 25 (e.g., an ultraviolet or near ultraviolet source such as a mercury arc lamp), an optional filter 26 to receive the output beam 27 from the source 25 and selectively pass only the desired wavelengths (e.g., the 365 nm Hg line), and a condenser lens 28 for forming a collimated beam 30. Other devices for filtering or monochromating the source light, e.g., diffraction gratings, dichroic mirrors, and prisms, may also be used rather than a transmission filter, and are generically referred to as "filters" herein. The beam 30 is projected onto a beam splitter 32 which reflects a portion of the beam 30 into a beam 33 which is projected onto a two-dimensional micromirror array device 35. The micromirror array device 35 has a two-dimensional array of individual micromirrors 36 which are each responsive to control signals supplied to the array device 35 to tilt in one of at least two directions. Control signals are provided from a computer controller 38 on control lines 39 to the micromirror array device 35. The micromirrors 36 are constructed so that in a first position of the mirrors the portion of the incoming beam of light 33 that strikes an individual micromirror 36 is deflected in a direction oblique to the incoming beam 33, as indicated by the arrows 40. In a second position of the mirrors 36, the light from the beam 33 striking such mirrors in such second position is reflected back parallel to the beam 33, as indicated by the arrows 41. The light reflected from each of the mirrors 36 constitutes an individual beam 41. The multiple beams 41 are incident upon the beam splitter 32 and pass through the beam splitter with reduced intensity and are then incident upon projection optics 44 comprised of, e.g., lenses 45 and 46 and an adjustable iris 47. The projection optics 44 serve to form an image of the pattern of the micromirror array 35, as represented by the individual beams 41 (and the dark areas between these beams), on the active surface 15 of the substrate 12. The outgoing beams 41 are directed along a main optical axis of the image former 11 that extends between the micromirror device and the substrate. The substrate 12 in the configuration shown in FIG. 1 is transparent, e.g., formed of fused silica or soda lime glass or quartz, so that the light projected thereon, illustratively represented by the lines labeled 49, passes through the substrate 12 without substantial attenuation or diffusion.

A preferred micromirror array 35 is the Digital Micromirror Device (DMD) available commercially from Texas Instruments, Inc. These devices have arrays of micromirrors (each of which is substantially a square with edges of 10 to 20 μm in length) which are capable of forming patterned beams of light by electronically addressing the micromirrors in the arrays. Such DMD devices are typically used for video projection and are available in various array sizes, e.g., 640×800 micromirror elements (512,000 pixels), 640×480 (VGA; 307,200 pixels), 800×600 (SVGA; 480,000 pixels); and 1024×768 (786,432 pixels). Such arrays are discussed in the following article and patents: Larry J. Hornbeck, "Digital Light Processing and MEMs: Reflecting the Digital Display Needs of the Networked Society," SPIE/EOS European Symposium on Lasers, Optics, and Vision for Productivity and Manufacturing I, Besancon, France, Jun. 10–14, 1996; and U.S. Pat. Nos. 5,096,279, 5,535,047, 5,583,688 and 5,600,383. The micromirrors 36 of such devices are capable of reflecting the light of normal usable wavelengths, including ultraviolet and near ultraviolet light, in an efficient manner without damage to the mirrors themselves.

The window of the enclosure for the micromirror array preferably has anti-reflective coatings thereon optimized for the wavelengths of light being used. Utilizing commercially available 600×800 arrays of micromirrors, encoding 480,000 pixels, with typical micromirror device dimensions of 16 microns per mirror side and a pitch in the array of 17 microns, provides total micromirror array dimensions of 13,600 microns by 10,200 microns. By using a reduction factor of 5 through the optics system 44, a typical and readily achievable value for a lithographic lens, the dimensions of the image projected onto the substrate 12 are thus about 2,220 microns by 2040 microns, with a resolution of about 2 microns. Larger images can be exposed on the substrate 12 by utilizing multiple side-by-side exposures (by either stepping the flow cell 18 or the image projector 11), or by using a larger micromirror array. It is also possible to do one-to-one imaging without reduction as well as enlargement of the image on the substrate, if desired.

The projection optics 44 may be of standard design, since the images to be formed are relatively large and well away from the diffraction limit. The lenses 45 and 46 focus the light in the beam 41 passed through the adjustable iris 47 onto the active surface of the substrate. The projection optics 44 and the beam splitter 32 are arranged so that the light deflected by the micromirror array away from the main optical axis (the central axis of the projection optics 44 to which the beams 41 are parallel), illustrated by the beams labeled 40 (e.g., 10° off axis) fall outside the entrance pupil of the projection optics 44 (typically 0.5/5=0.1; 10° corresponds to an aperture of 0.17, substantially greater than 0.1). The iris 47 is used to control the effective numerical aperture and to ensure that unwanted light (particularly the off-axis beams 40) are not transmitted to the substrate. Resolution of dimensions as small as 0.5 microns are obtainable with such optics systems. For manufacturing applications, it is preferred that the micromirror array 35 be located at the object focal plane of a lithographic I-line lens optimized for 365 nm. Such lenses typically operate with a numerical aperture (NA) of 0.4 to 0.5, and have a large field capability The micromirror array device 35 may be formed with a single line of micromirrors (e.g., with 2,000 mirror elements in one line) which is stepped in a scanning system. In this manner the height of the image is fixed by the length of the line of the micromirror array but the width of the image that may be projected onto the substrate 12 is essentially unlimited. By moving the stage 18 which carries the substrate 12, the mirrors can be cycled at each indexed position of the substrate to define the image pattern at each new line that is imaged onto the substrate active surface.

Various approaches may be utilized in the fabrication of the DNA probes 16 on the substrate 12, and are adaptations of microlithographic techniques. In a "direct photofabrication approach," the glass substrate 12 is coated with a layer of a chemical capable of binding the nucleotide bases. Light is applied by the projection system 11, deprotecting the OH groups on the substrate and making them available for binding to the bases. After development, the appropriate nucleotide base is flowed onto the active surface of the substrate and binds to the selected sites using normal phosphoramidite DNA synthesis chemistry. The process is then repeated, binding another base to a different set of locations. The process is simple, and if a combinatorial approach is used the number of permutations increases exponentially. The resolution limit is presented by the linear response of the deprotection mechanism. Because of the limitations in resolution achievable with this method, methods based on photoresist technology may be used instead, as described, e.g., in McGall, et al., supra. In the indirect photofabrication approach, compatible chemistries exist with a two-layer resist system, where a first layer of, e.g., polyimide acts as a protection for the underlying chemistry, while the top imaging resist is an epoxy-based system. The imaging step is common to both processes, with the main requirement being that the wavelength of light used in the imaging process be long enough not to excite transitions (chemical changes) in the nucleotide bases (which are particularly sensitive at 280 nm). Hence, wavelengths longer than 300 nm should be used. 365 nm is the I-line of mercury, which is the one used most commonly in wafer lithography.

Figure 2:
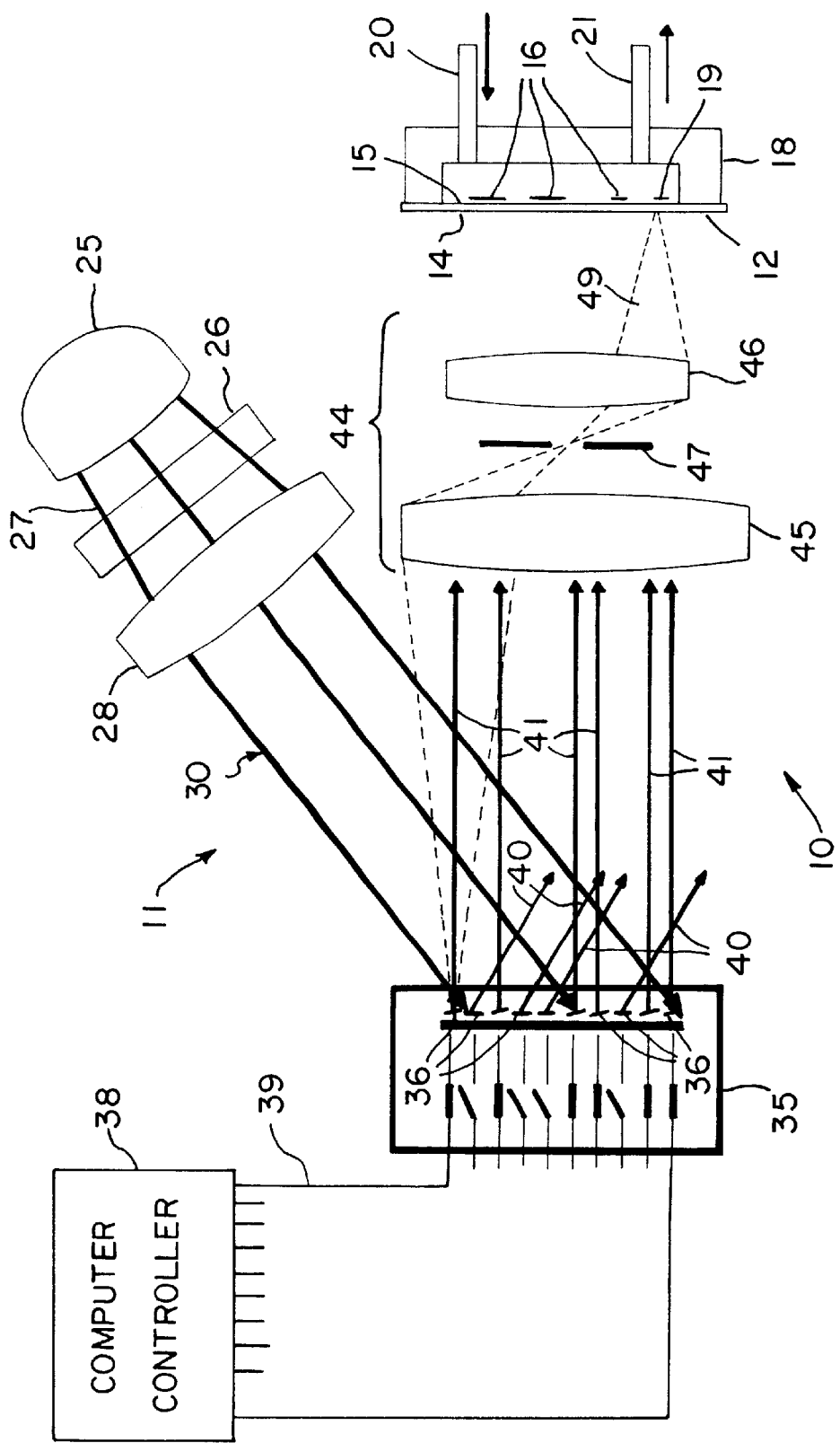
FIG. 2 is a schematic view of another array synthesizer apparatus in accordance with the present invention.

Another form of the array synthesizer apparatus 10 is shown in a simplified schematic view in FIG. 2. In this arrangement, the beamsplitter 32 is not used, and the light source 25, optional filter 26, and condenser lens 28 are mounted at an angle to the main optical axis (e.g., at 20° to the axis) to project the beam of light 30 onto the array of micromirrors 36 at an angle. The micromirrors 36 are oriented to reflect the light 30 into off axis beams 40 in a first position of the mirrors and into beams 41 along the main axis in a second position of each mirror. In other respects, the array synthesizer of FIG. 2 is the same as that of FIG. 1.

Figure 3:
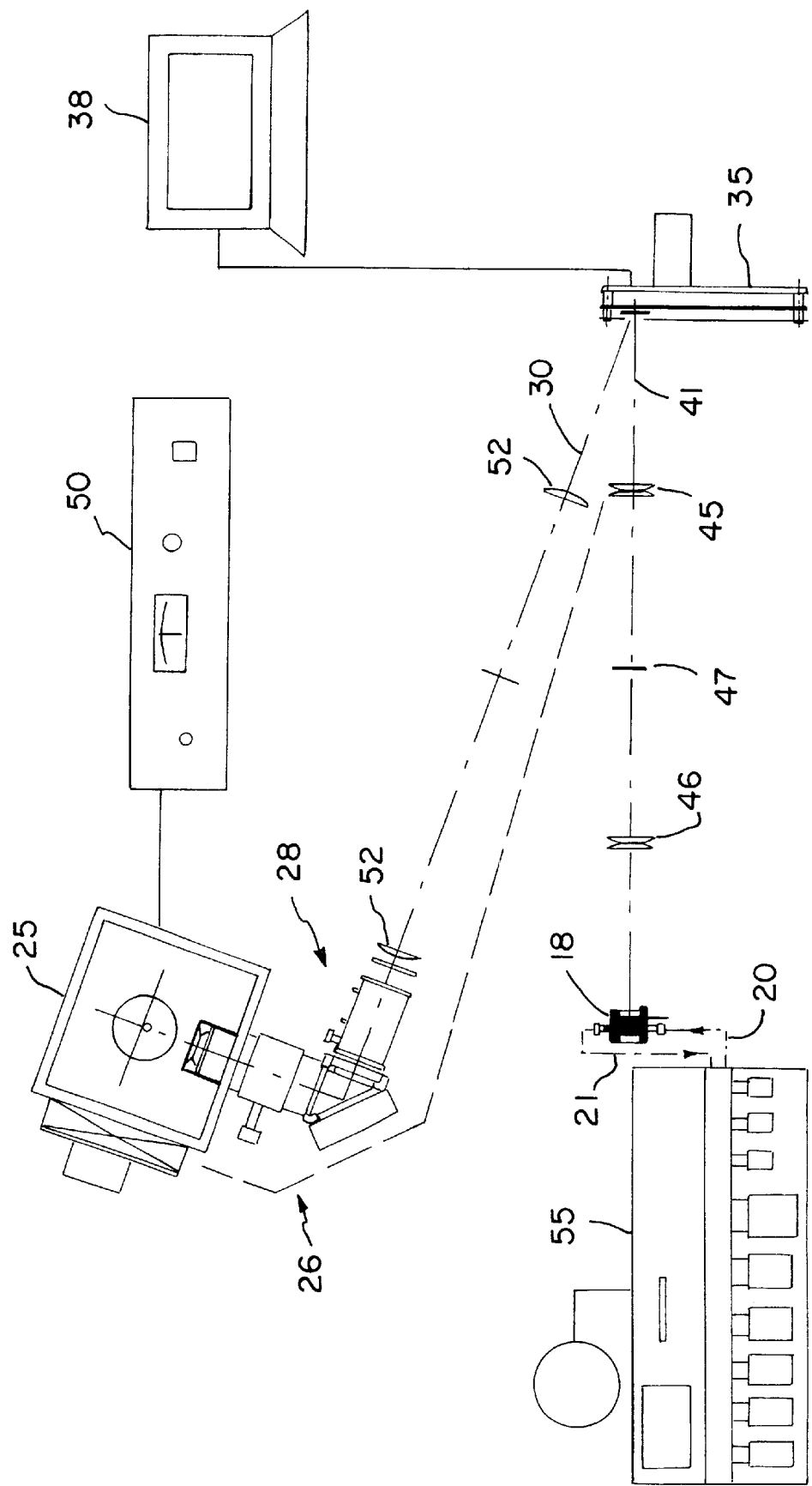
FIG. 3 is a more detailed schematic view of a general telecentric array synthesizer apparatus in accordance with the invention.
Figure 4:
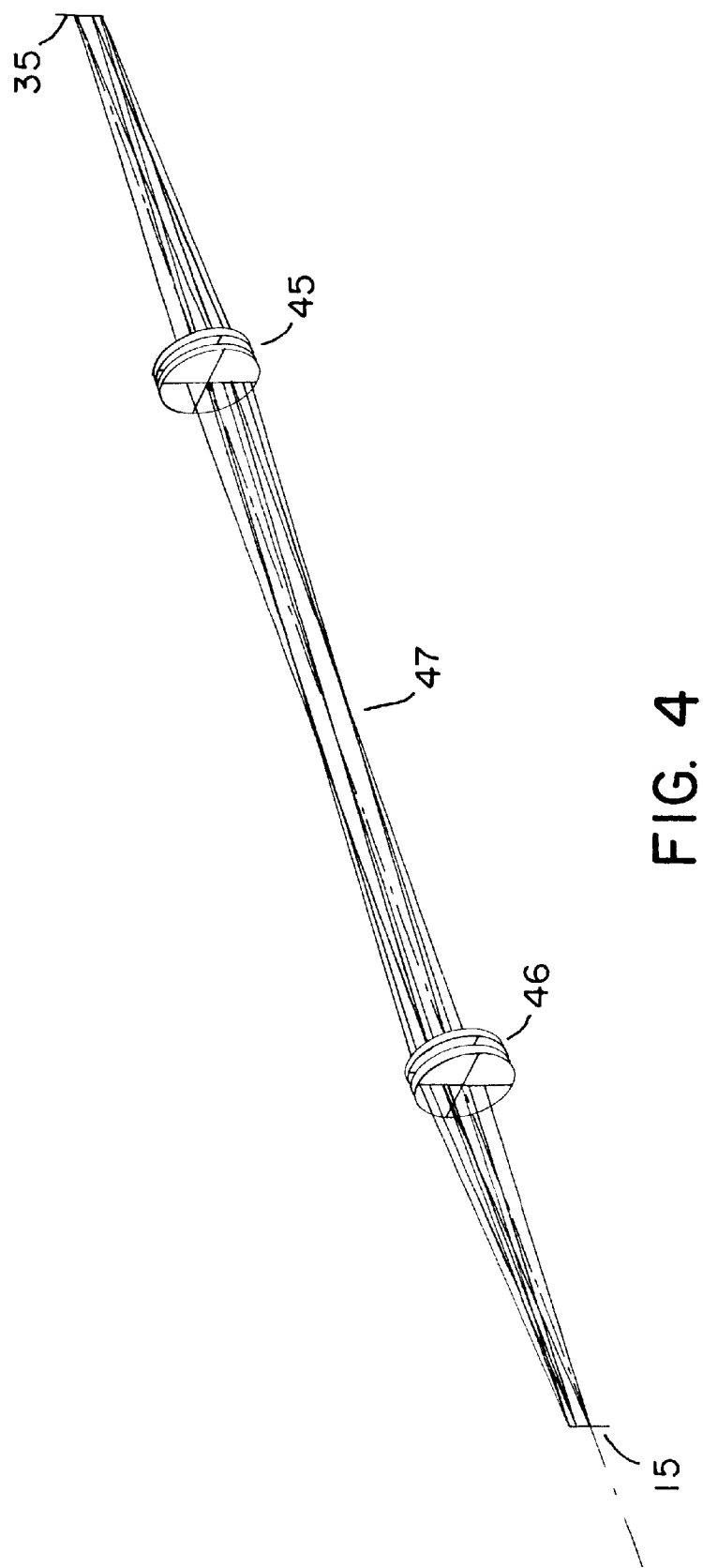
FIG. 4 is an illustrative ray diagram for the refractive optics of the apparatus of FIG. 3.

A more detailed view of a preferred array synthesizer apparatus which uses the off-axis projection arrangement of FIG. 2 is shown in FIG. 3. In the apparatus of FIG. 3, the source 25 (e.g., 1,000 W Hg arc lamp, Oriel 6287, 66021), provided with power from a power supply 50 (e.g., Oriel 68820), is-used as the light source which contains the desired ultraviolet wavelengths. The filter system 26 is composed, for example, of a dichroic mirror (e.g., Oriel 66226) that is used to absorb infrared light and to selectively reflect light of wavelengths ranging from 280 to 400 nm. A water-cooled liquid filter (e.g., Oriel 6127) filled with deionized water is used to absorb any remaining infrared. A colored glass filter (Oriel 59810) or an interference filter (Oriel 56531) is used to select the 365 nm line of the Hg lamp 25 with a 50% bandwidth of either 50 nm or 10 nm, respectively. An F/1 two element fused silica condenser (Oriel 66024) is used as the condenser 28, and with two plano-convex lenses 52 (Melles Griot 01LQP033 and Melles Griot 01LQP023), forms a Kohler illumination system. This illumination system produces a roughly collimated uniform beam 30 of 365 nm light with a diameter just large enough to encompass the 16 mm×12 mm active area of the micromirror array device 35. This beam 30 is incident onto the device 35 at an angle of 20° measured from the normal to the face of the device. The micromirror array device 35 is located approximately 700 mm away from the last filter. When the micromirrors are in a first position, the light in the beam 30 is deflected downwardly and out of the system. For example, in this micromirror device the mirrors in their first position may be at an angle of −10° with respect to the normal to the plane of the micromirrors to reflect the light well away from the optical axis. When a micromirror is controlled to be deflected in a second position, e.g., at an angle of +10° with respect to the normal to the plane of the micromirrors, the light reflected from such micromirrors in the second position emerges perpendicularly to the plane of the micromirror array in the beam 41. The pattern formed by the light reflected from the micromirrors in their second position is then imaged onto the active surface 15 of a glass substrate 12 enclosed in a flow cell 18 using a telecentric imaging system composed of two doublet lenses 45 and 46 and an adjustable aperture 47. Each of the doublet lenses 45 and 46 is composed of a pair of plano-convex lenses (e.g., Melles Griot 01LQP033 and 01LQP037) put together with the curved surfaces nearly touching. The first doublet lens is oriented so that the shorter focal length (01LQP033) side is towards the micromirror array device 35, and the second doublet is oriented so that its longer focal length (01LQP037) side is toward the micromirror array device 35. Doublets composed of identical lenses may be used, in which case either side may face the micromirror array device. The adjustable aperture 47, also called a telecentric aperture, is located at the back focal plane of the first doublet. It is used to vary the angular acceptance of the optical system. Smaller aperture diameters correspond to improve contrast and resolution but with correspondingly decreased intensity in the image. As illustrated in FIG. 3, a standard DNA synthesizer 55 supplied with the requisite chemicals can be connected by the tubes 20 and 21 to the flow cell 18 to provide the desired sequence of chemicals, either under independent control or under control of the computer 38. A typical diameter for the aperture 47 is about 30 nm. An illustrative ray diagram showing the paths of light through the lenses 45 and 46 is shown in FIG. 4 for this type of refractive optical system. Fans of rays originating at the center of the object (the micromirror device face), at the edge, and at an intermediate location are shown. The optical system forms an inverted image of the face of the micromirror array device.

Figure 5:
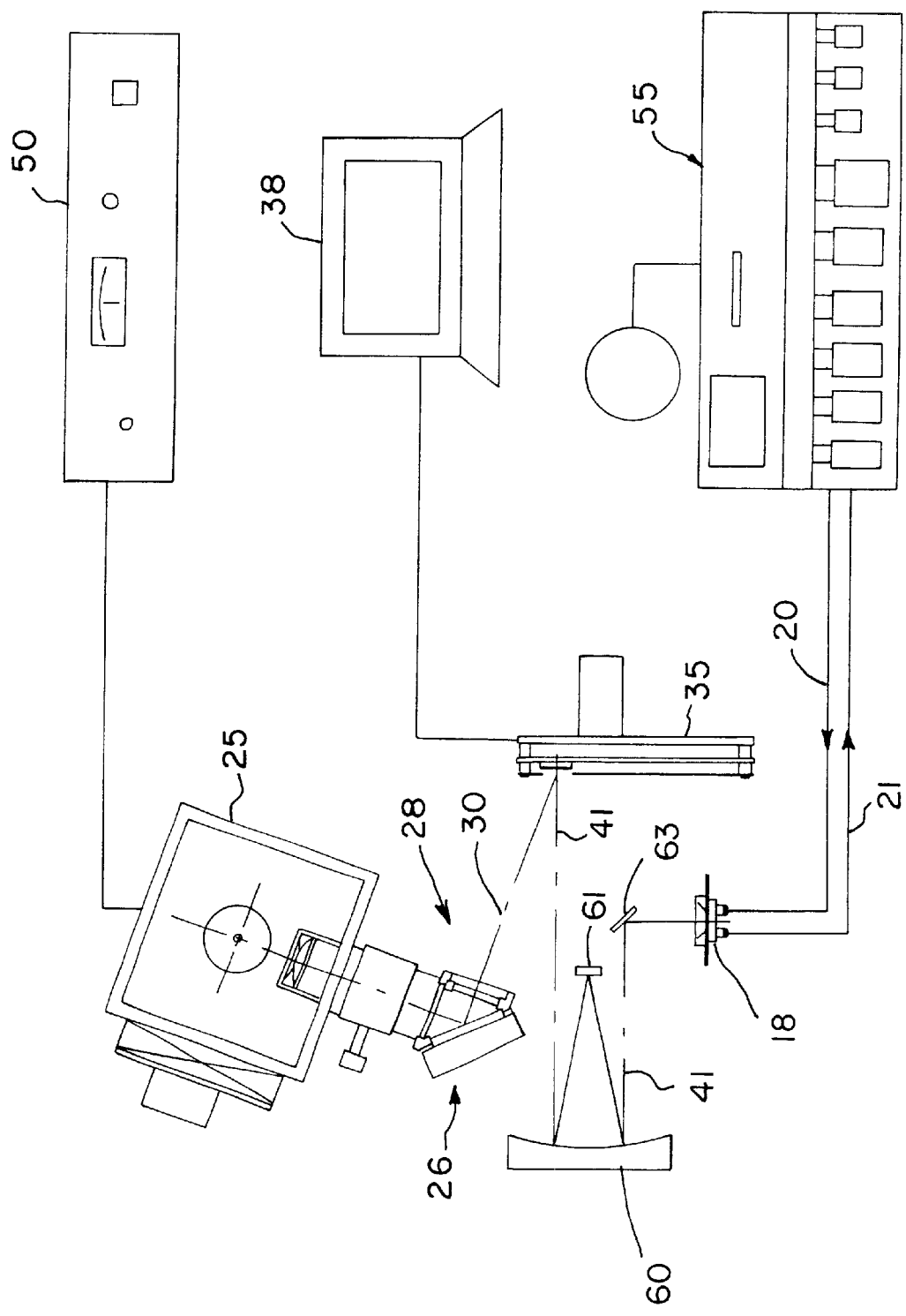
FIG. 5 is a schematic view of a further embodiment of an array synthesizer apparatus in accordance with the invention in which telecentric reflective optics are utilized.

Another embodiment of the array synthesizer apparatus using reflective optics is shown in FIG. 5. An exemplary system utilizes a 1,000 W Hg arc lamp 25 as a light source (e.g., Oriel 6287, 66021), with a filter system formed of a dichroic mirror (e.g., Oriel 66228) that absorbs infrared light and selectively reflects light of wavelengths ranging from 350 to 450 nm. An F/1 two element fused silica condenser lens (Oriel 66024) is used to produce a roughly collimated beam of light 30 containing the 365 nm line but excluding undesirable wavelengths around and below 300 nm. A Kohler illumination system may optionally also be used in the apparatus of FIG. 5 to increase uniformity and intensity. The beam 30 is incident onto the micromirror array device 35 which has an active area of micromirrors of about 16 mm×12 mm and which is located about 210 nm from the snout of the UV source 25, with the beam 30 striking the planar face of the micromirror device 35 at an angle of 20° with respect to a normal to the plane of the array. The light reflected from the micromirrors in a first position of the micromirrors, e.g., −10° with respect to the plane of the array, is directed out of the system, whereas light from micromirrors that are in a second position, e.g., +10° with respect to the plane of the array, is directed in the beam 41 toward a reflective telecentric imaging system composed of a concave mirror 60 and a convex mirror 61. Both mirrors are preferably spherical and have enhanced UV coating for high reflectivity. After executing reflections from the mirrors 60 and 61, the beam 41 may be incident upon another planar mirror 63 which deflects the beam toward the flow cell 18. The light reflected from the micromirrors is imaged onto the active surface of a glass substrate enclosed in the flow cell 18. A telecentric aperture (not shown in FIG. 5) may be placed in front of the convex mirror. The beam 41 first strikes the concave mirror, then the convex mirror, and then the concave mirror again, with the planar mirror 63 optionally being used to deflect the light 90° to direct it to the flow cell 18. For the system shown, the concave mirror 60 may have a diameter of 152.4 mm, and a spherical mirror surface radius of 304.8 mm (ES F43561), and the convex mirror may have a diameter of 25 mm, and a spherical mirror surface radius of 152.94 mm (ES F45625). Ideally, the radius of curvature of the concave mirror is twice that of the convex mirror. Such reflective optical systems are well known and conventionally used in optical lithography in "MicroAlign" type systems. See, e.g., A. Offner, "New Concepts in Projection Mask Aligners," Optical Engineering, Vol. 14, pp. 130–132 (1975), and R. T. Kerth, et al., "Excimer Laser Projection Lithography on a Full- Field Scanning Projection System," IEEE Electron Device Letters, Vol. EDL-7(5), pp. 299–301 (1986).

Figure 6:
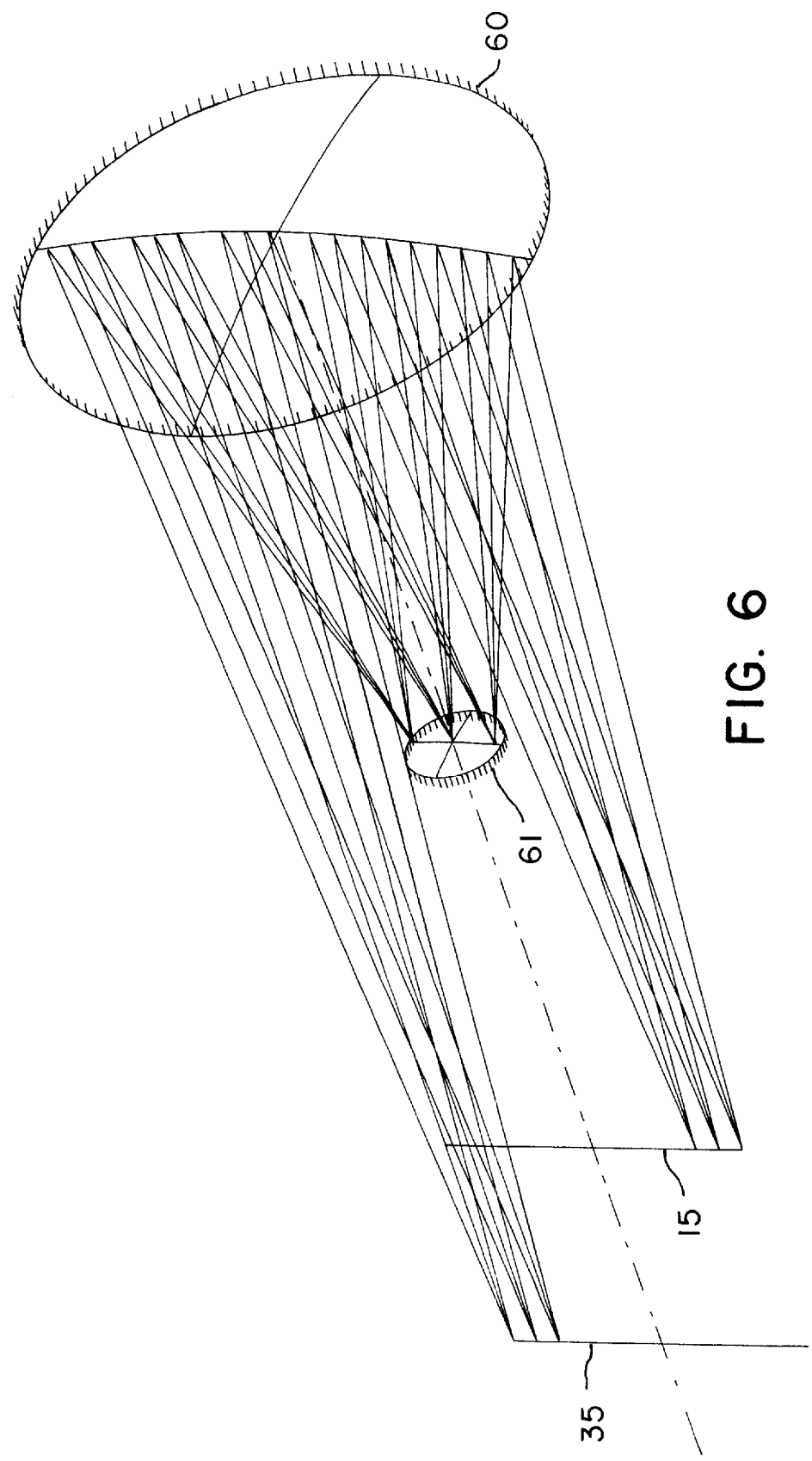
FIG. 6 is an illustrative ray diagram for the reflective optics of the apparatus of FIG. 5.

FIG. 6 illustrates image formation for the optical system of FIG. 5. Fans of rays originating in the center of the object (the micromirror array device), at the edge, and at an intermediate position are shown in FIG. 6. The rays reflect first from the concave mirror 60, then from the convex mirror 61, then from the concave mirror 60 again, to form an inverted image of the face of the micromirror array device. The planar mirror 63 is not included in the diagram of FIG. 6. A telecentric aperture (not shown) may be placed in front of the convex mirror.

The refractive or reflective optical systems are both preferably "symmetric" to minimize aberrations such as coma and spherical aberration via cancellation. The foregoing reflective system has a higher numerical aperture which yields higher intensity. Both of the telecentric optical systems of FIGS. 3 and 5 are 1:1 imaging systems. A reflective system has the potential advantages of eliminating chromatic aberration and providing higher resolution, as well as being compact and less expensive. A preferred system for doing 1:1 imaging would be a Wynne-Dyson type system which combines concave mirror with lenses and prisms. It has a very high numerical aperture which enhances intensity. See, e.g., F. N. Goodall, et al., "Excimer Laser Photolithography with 1:1 Wynne-Dyson Optics," SPIE Vol. 922, Optical/Laser Microlithography, 1988; and B. Ruff, et al., "Broadband Deep-UV High NA Photolithography System," SPIE Vol. 1088, Optical/Laser Microlithography II (1989).

Figure 7:
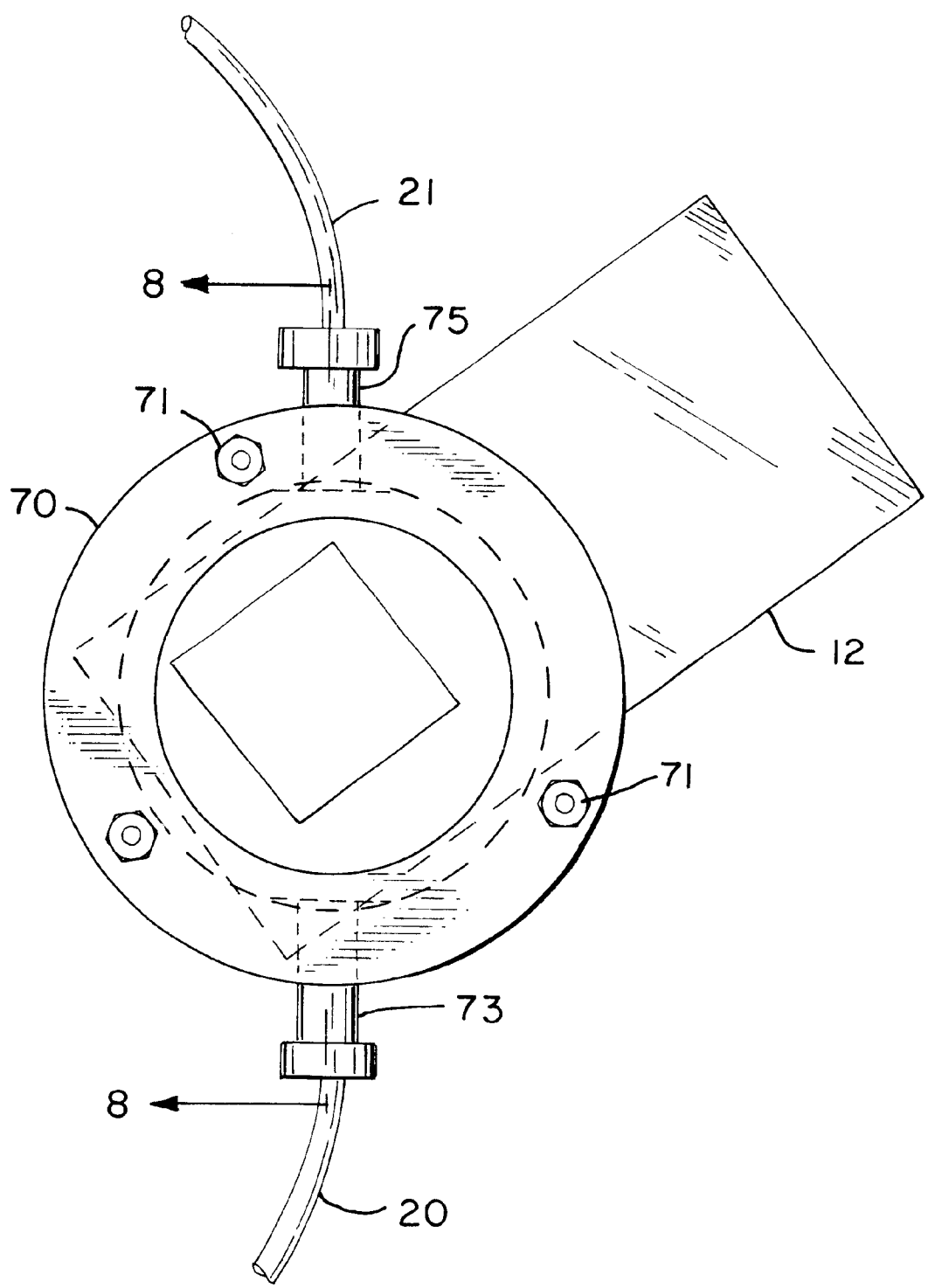
FIG. 7 is a top plan view of a reaction chamber flow cell which may be utilized in the array synthesizer apparatus of the invention.
Figure 8:
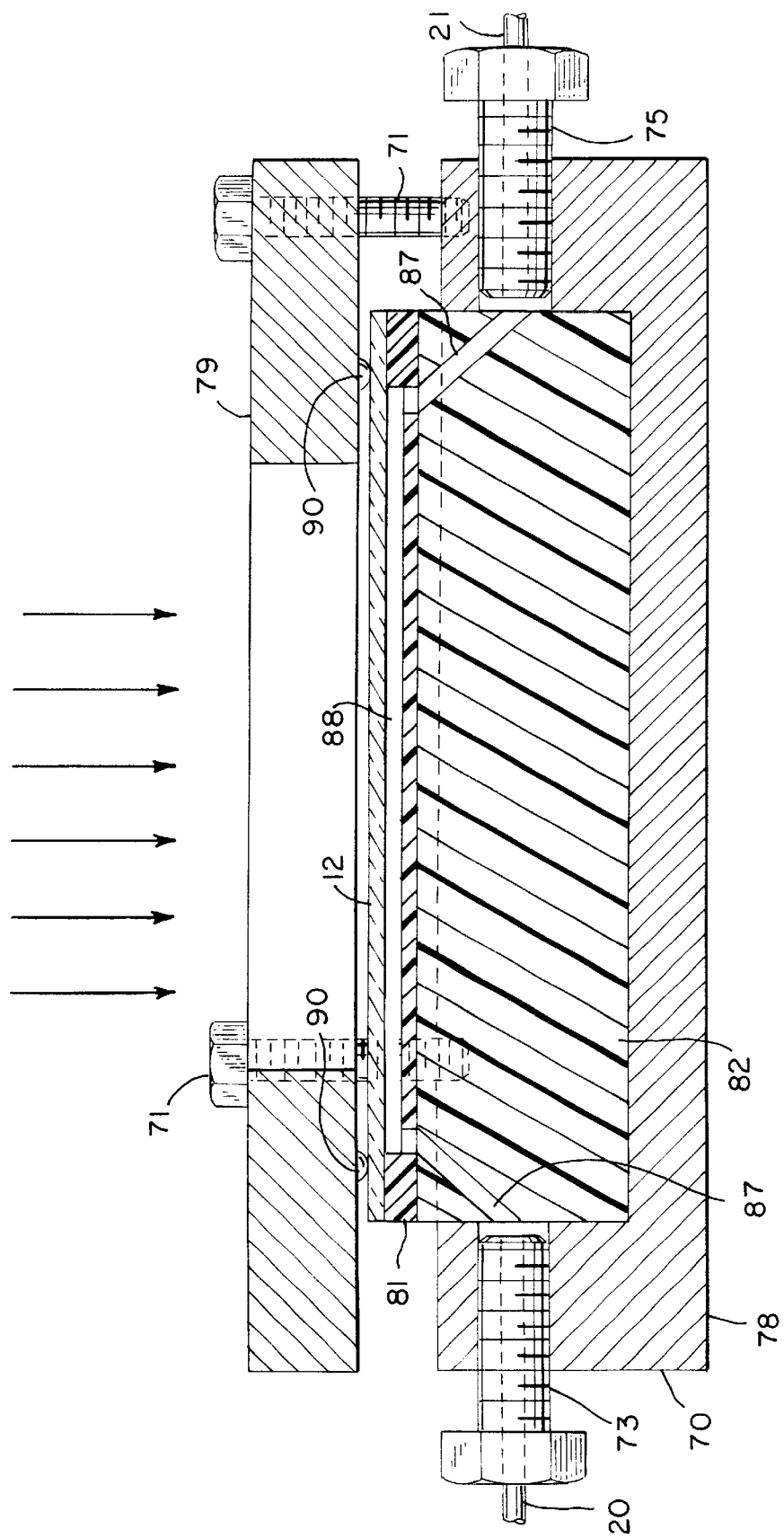
FIG. 8 is a cross-sectional view through the reaction chamber flow cell of FIG. 7 taken generally along the lines 8—8 of FIG. 7.

More detailed views of a reaction chamber flow cell 18 that may be utilized with the apparatus of the invention is shown in FIGS. 7 and 8. The exemplary flow cell 18 in these figures includes an aluminum housing 70, held together by bolts 71, having an inlet 73 connected to an input port line 20 and an outlet 75 converted to an output port line 21. As illustrated in the cross-sectional view of FIG. 8, the housing 70 includes a lower base 78 and an upper cover section 79 which are secured together over the substrate with the bolts 71. The substrate 12, e.g., a transparent glass slide, is held between the upper plate 79 and a cylindrical gasket 81 (e.g., formed of Kal ReZ™), which in turn is supported on a nonreactive base block 82 (e.g., Teflon™), with an inlet channel 85 extending from the inlet 73 to a sealed reaction chamber 88 formed between the substrate 12 and the base block 82 that is sealed by the gasket, and with an outlet channel 89 extending from the reaction chamber 88 to the outlet 75. The bolts 71 can be screwed and unscrewed to detachably secure the substrate 12 between the cover section and the base to allow the substrate to be replaced with minimal displacement of the base of the flow cell. Preferably, as shown in FIG. 8, a rubber gasket 90 is mounted at the bottom of the plate 79 to engage against the substrate at a peripheral region to apply pressure to the substrate against the gasket 81. If desired, the flow cell may also be used as a hybridization chamber during readout.

Figure 9:
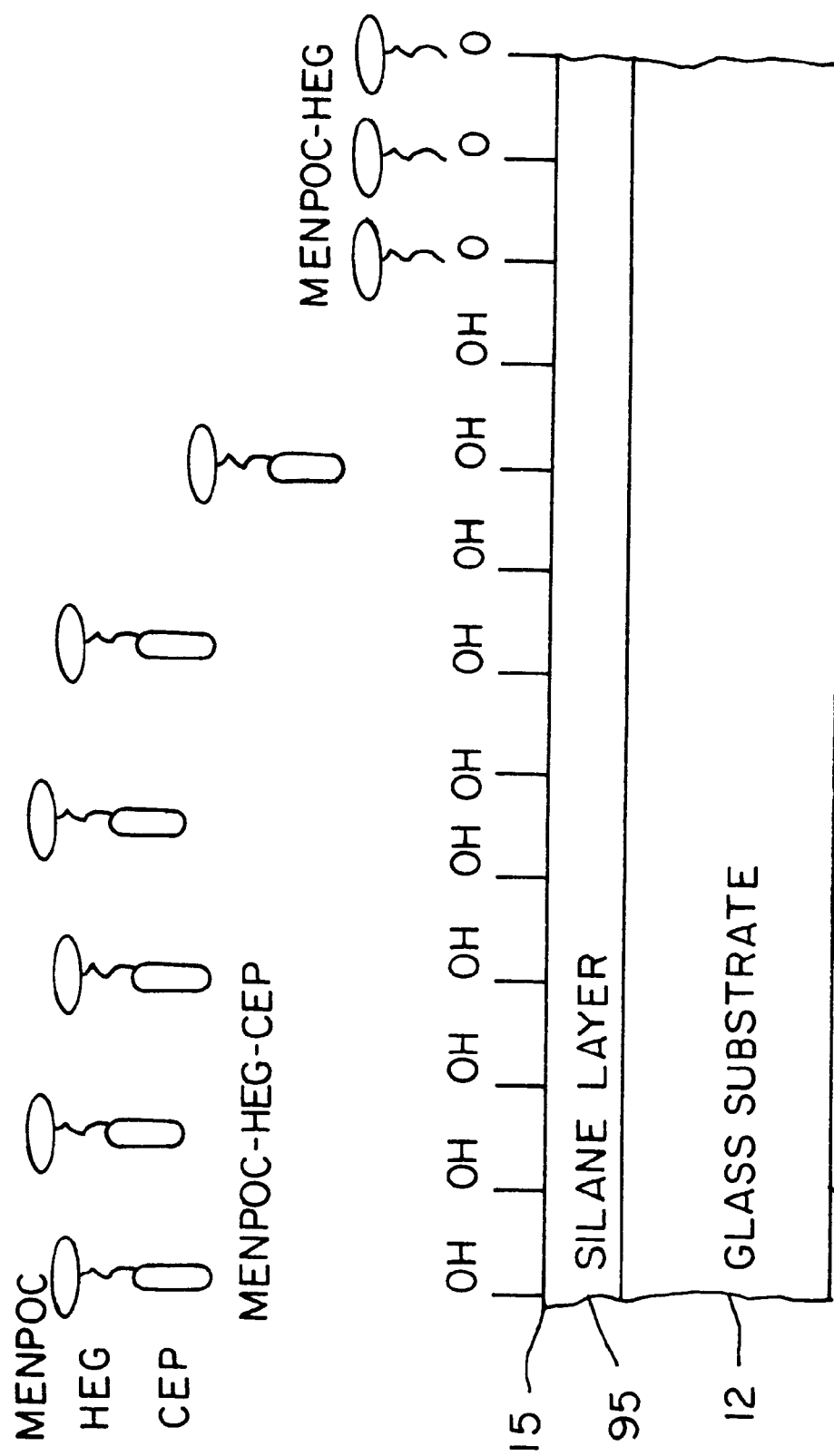
FIG. 9 is an illustrative view showing the coating of a substrate with a photolabile linker molecule.

An exemplary process for forming DNA probes is illustrated with respect to the schematic diagrams of FIGS. 9–14. FIG. 9 illustrates the coating of the substrate 12, having a silane layer 95 forming the active surface 15 thereof, with the photolabile linker molecule MENPOC-HEG coated on the silane layer using standard phosphoramidite chemistry. MENPOC-HEG-CEP=18-O-[(R,S)-(1-(3,4-(Methylenedioxy)-6-nitrophenyl)ethoxy)carbonyl]-3,6,9,12,15,18-hexaoxaoctadec-1-yl O'-2-cyanoethyl-N,N-Diisopropylphosphoramidite. The silane layer was made from N(3-(triethoxysilyl)-propyl)-4-hydroxybutyramide. At the step shown in FIG. 9, the substrate can be exposed to light and active free OH groups will be exposed in areas that have been exposed to light.

Figure 10:
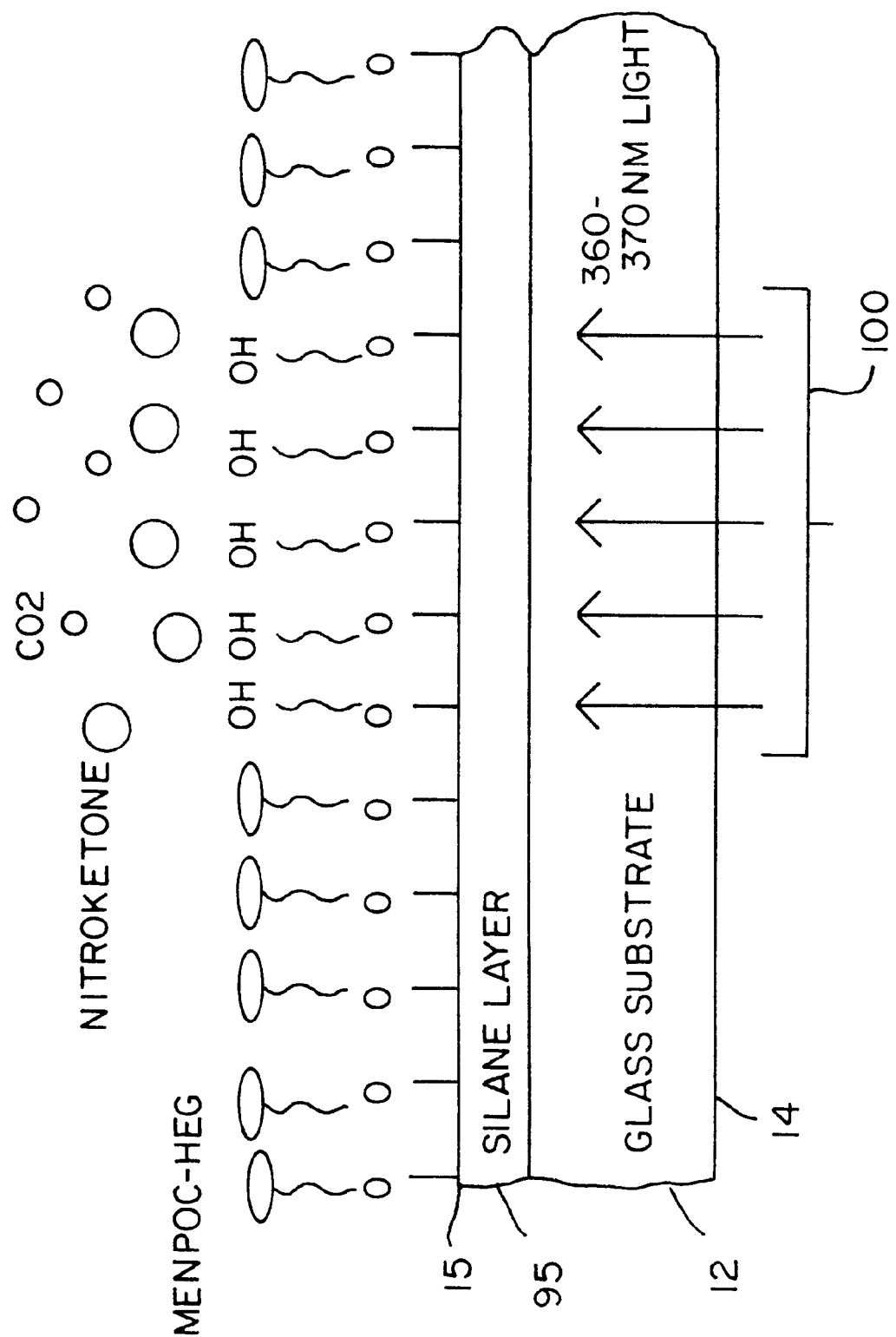
FIG. 10 is an illustrative view showing the photo-deprotection of the linker molecule and the production of free OH groups.
Figure 11:
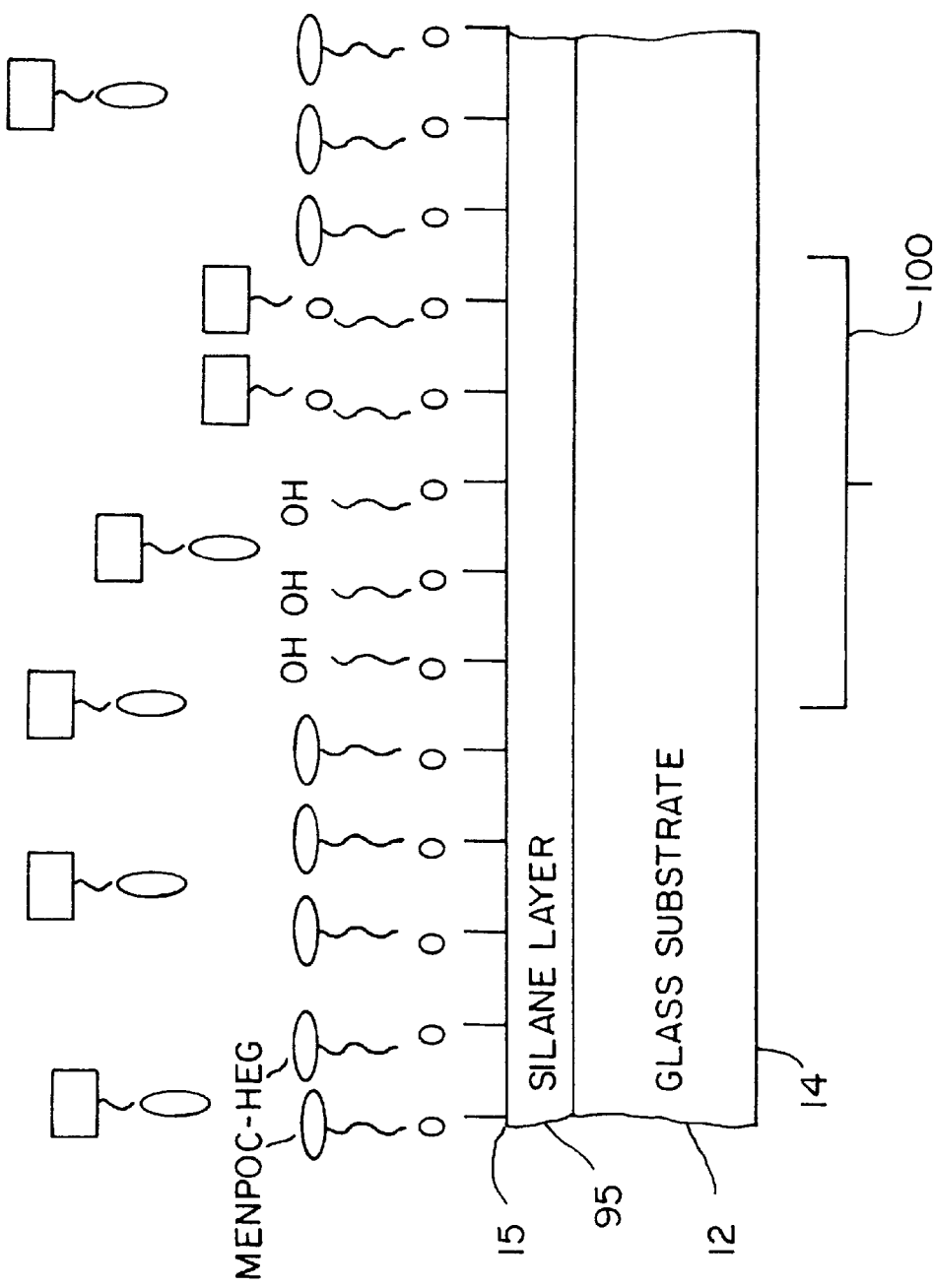
FIG. 11 is an illustrative view showing the coupling of markers to free OH groups produced by the photo-deprotection of the linker molecules.
Figure 12:
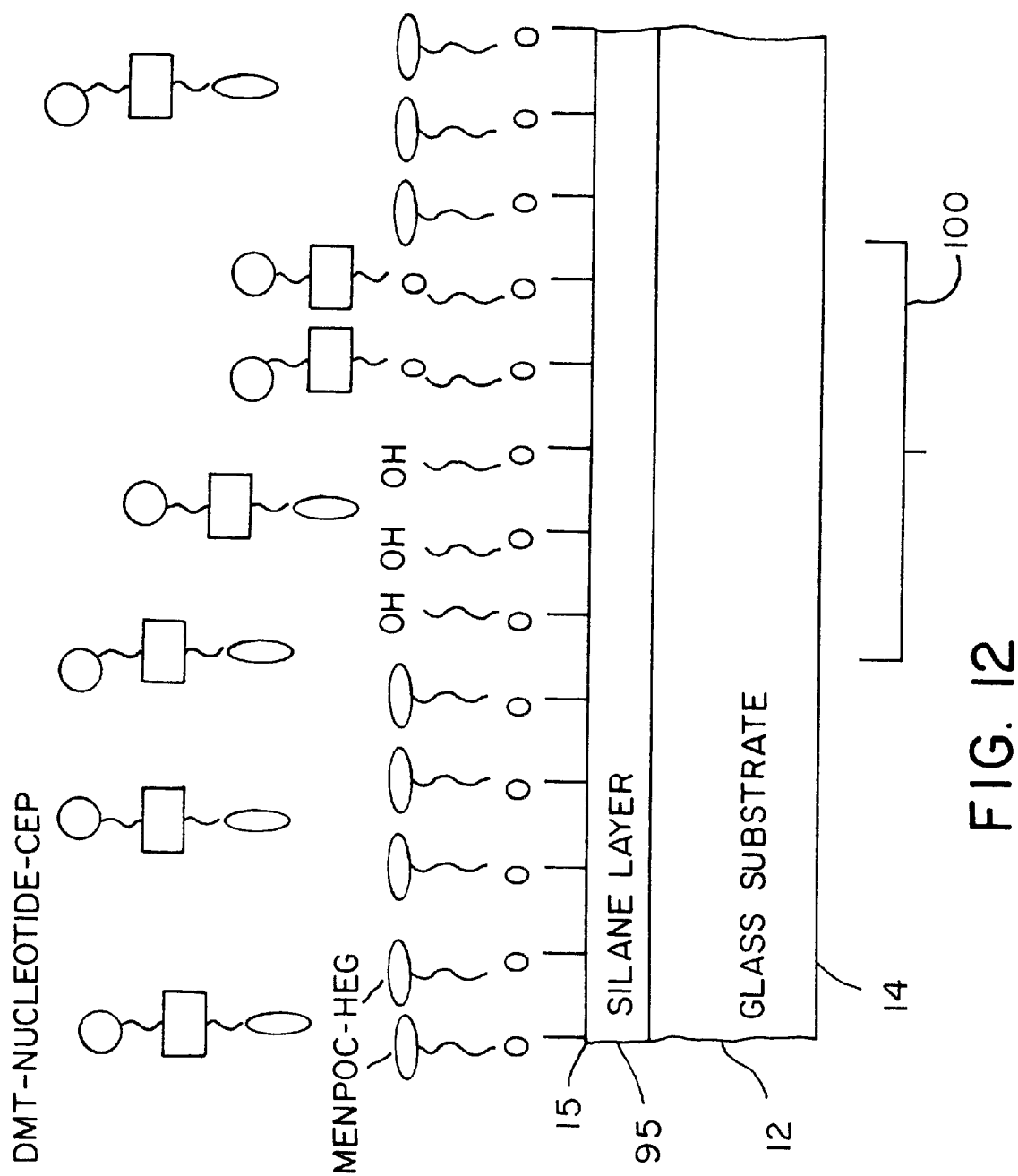
FIG. 12 is an illustrative view showing the coupling of DMT-nucleotide to free OH groups produced from photo-deprotection of the linker molecules.
Figure 13:
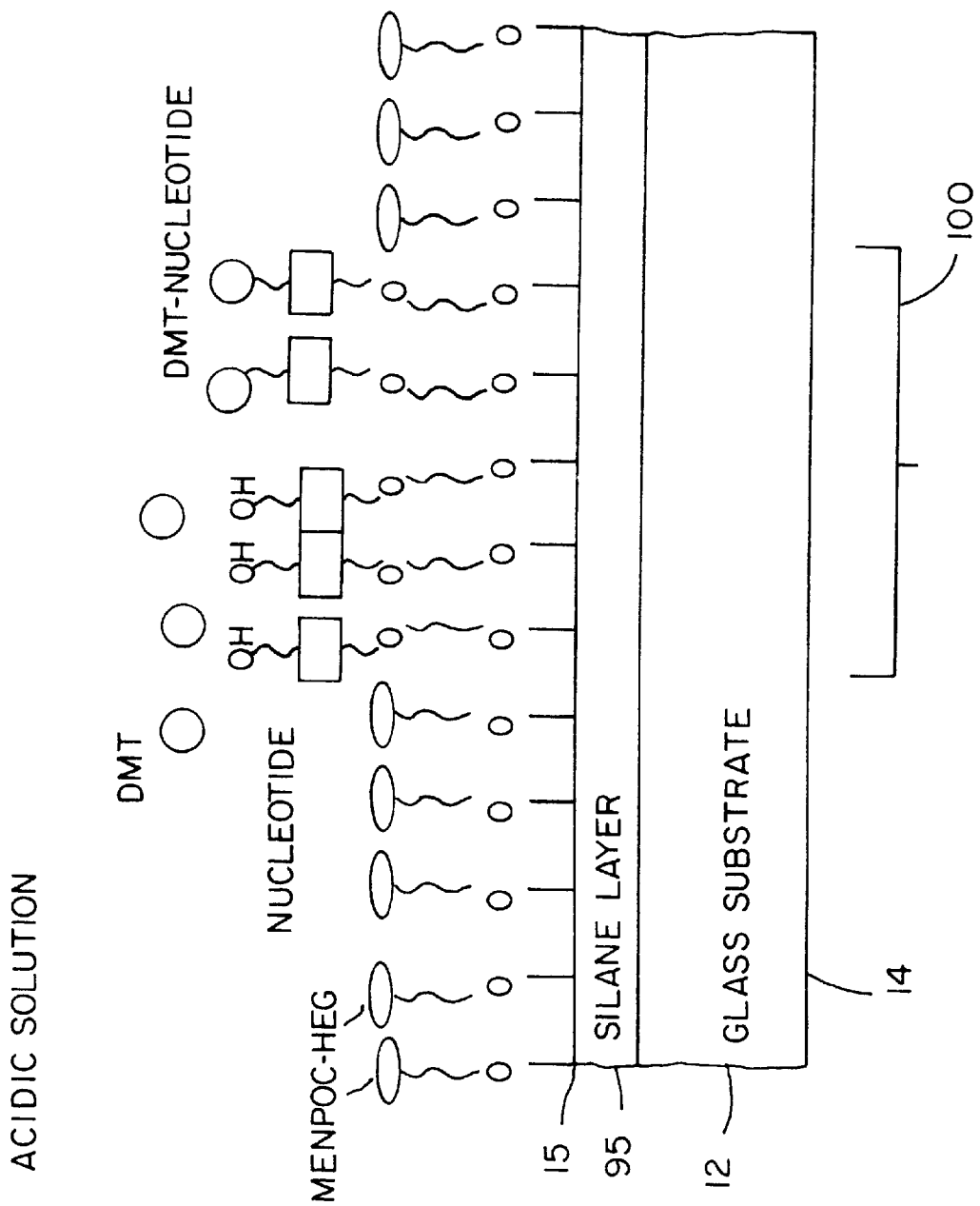
FIG. 13 is an illustrative view showing acid deprotection of DMT-nucleotides.
Figure 14:
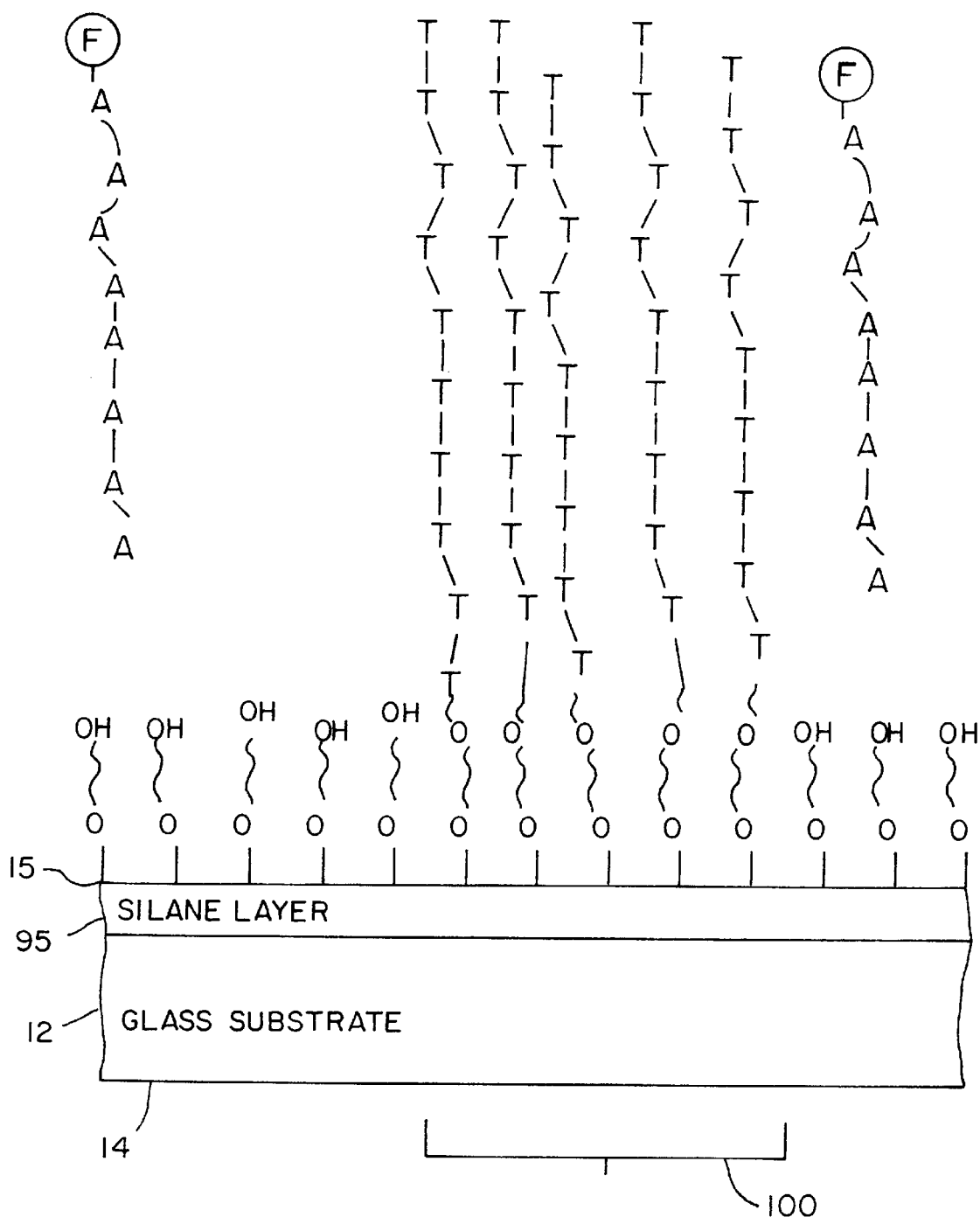
FIG. 14 is an illustrative view showing the hybridization of poly-A probe labeled with fluorescein with poly-T oligo-nucleotide synthesized from DMT-nucleotide-CEPs.

FIG. 10 illustrates the photo-deprotection of the MENPOC-HEG linker and the production of free OH groups in the area 100 that is exposed to light. FIG. 11 illustrates the coupling of FluorePrime™ fluorescein amidite to free OH groups produced from photo-deprotection of MENPOC-HEG. FIG. 12 illustrates the coupling of DMT-nucleotide to free OH groups produced from photo-deprotection of MENPOC-HEG linker. FIG. 13 illustrates the step of acid deprotection of DMT-nucleotides in the area 100 exposed to light. FIG. 14 illustrates the hybridization of poly-A probe labeled with fluorescein with poly-T oligonucleotides synthesized from DMT-nucleotide-CEPs.

It is understood that the invention is not confined to the particular embodiments set forth herein as illustrative, but embraces all such modified forms thereof as come within the scope of the following claims.

What is claimed is:

1. Apparatus for use in synthesis of arrays of DNA probes, comprising:
   (a) a substrate with an active surface on which the arrays may be formed;
   (b) a flow cell enclosing the active surface of the substrate and having ports for applying DNA synthesis reagents into the flow cell which can be flowed over the active surface of the substrate; and
   (c) an image former providing a high precision, two-dimensional light image projected onto the substrate active surface, comprising:
      (1) a light source providing a light beam;
      (2) a micromirror device receiving the light beam from the source and formed of an array of electronically addressable micromirrors, each of which can be selectively tilted between one of at least two separate positions, wherein in one of the positions of each micromirror the light from the source incident upon the micromirror is deflected away from an optical axis and in a second of the at least two positions of the micromirror the light is reflected along the optical axis; and
      (3) projection optics receiving the light reflected from the micromirrors along the optical axis and imaging the pattern of the micromirrors onto the active surface of the substrate, wherein the light is directed from the micromirror onto the active surface by reflective optical elements.

2. The apparatus of claim 1 wherein the micromirror device is formed of a two dimensional array of micromirrors.

3. The apparatus of claim 1 including a lens for collimating the beam from the light source to provide a collimated beam projected onto the micromirror array at an oblique angle to a main optical axis that extends from the micromirror array to the substrate, and wherein in one position of each micromirror the light is reflected along the optical axis through the projection optics to the substrate and in a second position of each micromirror the light from the source is reflected at an angle off the main axis of the projection system and away from the substrate.

4. The apparatus of claim 1 further including a filter receiving the light from the source and which selectively passes only desired wavelengths through to the micromirror array.

5. The apparatus of claim 1 wherein the substrate is transparent and light from the image former is passed through the transparent substrate to be imaged on the active surface of the substrate which is opposite to the surface which initially receives the light from the image former.

6. The apparatus of claim 1 further including a computer connected to the micromirror device to provide command signals to control the deflection of the mirrors in the micromirror array to provide a desired pattern for projection onto the substrate.

7. The apparatus of claim 1 wherein the light provided by the light source is in the range of ultraviolet to near ultraviolet wavelengths.

8. The apparatus of claim 7 including a filter receiving the light from the source which selectively passes wavelengths in the ultraviolet and near ultraviolet and blocks longer wavelengths including infrared.

9. The apparatus of claim 8 wherein the filter includes a dichroic mirror that reflects the selected wavelengths and passes the wavelengths to be blocked.

10. The apparatus of claim 1 wherein the pattern of the micromirrors that is imaged onto the active surface of the substrate is reduced in size with respect to the size of the array of micromirrors.

11. The apparatus of claim 1 wherein the projection optics is telecentric.

12. The apparatus of claim 1 wherein the reflective optical elements include a concave mirror and a convex mirror, the concave mirror reflecting light from the micromirror device to the convex mirror which reflects it back to the concave mirror which reflects the light to the substrate where it is imaged.

13. The apparatus of claim 12 including a planar mirror that reflects the light from the concave mirror to the substrate.

14. The apparatus of claim 1 including a flow cell having a housing composed of a lower base and upper cover section and a gasket mounted on the base, wherein the substrate is a transparent glass slide secured between the upper cover section and the base to define a sealed reaction chamber between the substrate and the base that is sealed by the gasket, and channels extending through the housing from the input port to the reaction chamber and from the reaction chamber to the output port, the active surface of the substrate facing the sealed reaction chamber.

15. The apparatus of claim 14 including means for detachably securing the substrate between the lower base and upper cover section to allow the substrate to be replaced.

16. Apparatus for use in synthesis arrays of DNA probes, comprising:
    (a) a substrate with an active surface on which the arrays may be formed;
    (b) a flow cell enclosing the active surface of the substrate and having ports for applying DNA synthesis reagents into the flow cell which can be flowed over the active surface of the substrate; and
    (c) an image former providing a high precision, two-dimensional light image projected onto the substrate active surface, comprising:
        (1) a light source providing a light beam;
        (2) a micromirror device receiving the light beam from the source and formed of an array of electronically addressable micromirrors, wherein the micromirror device is formed of a two dimensional array of micromirrors, each of which can be selectively tilted between one of at least two separate positions, wherein in one of the positions of each micromirror the light from the source incident upon the micromirror is deflected away from an optical axis and in a second of the at least two positions of the micromirror the light is reflected along the optical axis; and
        (3) projection optics receiving the light reflected from the micromirrors along the optical axis and imaging the pattern of the micromirrors onto the active surface of the substrate, wherein the projection optics is telecetric and wherein light is directed from the micromirrors to the active surface is by reflective optical elements.

17. The apparatus of claim 16 including a lens for collimating the beam from the light source to provide a collimated beam projected onto the micromirror array at an oblique angle to a main optical axis that extends from the micromirror array to the substrate, and wherein in one position of each micromirror the light is reflected along the optical axis through the projection optics to the substrate and in a second position of each micromirror the light from the source is reflected at an angle off the main axis of the projection system and away from the substrate.

18. The apparatus of claim 16 further including a filter receiving the light from the source and which selectively passes only desired wavelengths through to the micromirror array.

19. The apparatus of claim 16 wherein the substrate is transparent and light from the image former is passed through the transparent substrate to be imaged on the active surface of the substrate which is opposite to the surface which initially receives the light from the image former.

20. The apparatus of claim 16 further including a computer connected to the micromirror device to provide command signals to control the deflection of the mirrors in the micromirror array to provide a desired pattern for projection onto the substrate.

21. The apparatus of claim 16 wherein the light provided by the light source is in the range of ultraviolet to near ultraviolet wavelengths.

22. The apparatus of claim 21 including a filter receiving the light from the source which selectively passes wavelengths in the ultraviolet and near ultraviolet and blocks longer wavelengths including infrared.

23. The apparatus of claim 22 wherein the filter includes a dichroic mirror that reflects the selected wavelengths and passes the wavelengths to be blocked.

24. The apparatus of claim 16 wherein the pattern of the micromirrors that is imaged onto the active surface of the substrate is reduced in size with respect to the size of the array of micromirrors.

25. The apparatus of claim 16 including refractive lenses between the light source and the micromirror device that form a Kohler illumination system.

26. The apparatus of claim 16 wherein the reflective optical elements include a concave mirror and a convex mirror, the concave mirror reflecting light from the micromirror device to the convex mirror which reflects it back to the concave mirror which reflects the light to the substrate where it is imaged.

27. The apparatus of claim 26 including a planar mirror that reflects the light from the concave mirror to the substrate.

28. The apparatus of claim 16 wherein the flow cell has a housing composed of a lower base and upper cover section is a gasket mounted on the base, wherein the substrate is a transparent glass slide secured between the upper cover section and the base to define a sealed reaction chamber between the substrate and the base that is sealed by the gasket, and channels extending through the housing from the input port to the reaction chamber and from the reaction chamber to the output port, the active surface of the substrate facing the sealed reaction chamber.

29. The apparatus of claim 28 including means for detachably securing the substrate between the lower base and upper cover section to allow the substrate to be replaced.

30. The apparatus of claim 1 further including a DNA synthesizer connected to supply reagents to the flow cell.

31. The apparatus of claim 16 further including a DNA synthesizer connected to supply reagents to the flow cell.

* * * * *

UNITED STATES PATENT AND TRADEMARK OFFICE
CERTIFICATE OF CORRECTION

PATENT NO.   : 6,375,903 B1
DATED        : April 23, 2002
INVENTOR(S)  : Francesco Cerrina et al.

It is certified that error appears in the above-identified patent and that said Letters Patent is hereby corrected as shown below:

Title page,
Item [54], "METHOD AND" should be replaced with -- MICROMIRROR --.

Column 12,
Line 9, the "is" after "surface" should be deleted.

Signed and Sealed this

Twenty-fifth Day of March, 2003

JAMES E. ROGAN
*Director of the United States Patent and Trademark Office*